United States Patent [19]

Bisiaux

[11] Patent Number: 5,311,127
[45] Date of Patent: May 10, 1994

[54] METHOD AND APPARATUS FOR INSPECTING METAL TUBES EMPLOYING MAGNETICALLY INDUCED EDDY CURRENTS

[75] Inventor: Bernard Bisiaux, Valenciennes, France

[73] Assignee: Vallourec Industries, Boulogne Billancourt, France

[21] Appl. No.: 673,075

[22] Filed: Mar. 21, 1991

[30] Foreign Application Priority Data

Mar. 26, 1990 [FR] France ................. 90 04053

[51] Int. Cl.⁵ ................. G01R 33/12; G01N 27/72
[52] U.S. Cl. ................. 324/232; 324/242
[58] Field of Search ............... 324/232, 225, 243, 242

[56] References Cited

U.S. PATENT DOCUMENTS

| | | | |
|---|---|---|---|
| 2,744,233 | 5/1956 | Paivinen | 324/227 |
| 3,916,301 | 10/1975 | Vild et al. | 324/226 |
| 4,327,419 | 12/1960 | Tornblom et al. | 324/232 |
| 4,355,281 | 10/1982 | Toth et al. | 324/242 |
| 4,954,777 | 9/1990 | Klopfer et al. | 324/232 |

*Primary Examiner*—Walter E. Snow
*Attorney, Agent, or Firm*—Oblon, Spivak, McClelland, Maier & Neustadt

[57] ABSTRACT

The method and the apparatus relate to the detection of faults in the wall of a passing metal tube. A solenoid or solenoids generate two alternating magnetic fields of different frequenceis, the frequencies being chosen from the range of medium and high frequencies, in order to produce in the wall of a tube eddy currents which interact with the faults. The signals resulting from these interactions are detected by at least one detection solenoid and each difference in amplitude D between the signals obtained at the two frequencies for one and the same fault is compared with a specific difference which constitutes a threshold for rejection of the corresponding tube. Application of the method and of the apparatus to the inspection of ferrous or non-ferrous magnetic and non-magnetic metal tubes.

14 Claims, 3 Drawing Sheets

METHOD AND APPARATUS FOR INSPECTING METAL TUBES EMPLOYING MAGNETICALLY INDUCED EDDY CURRENTS

BACKGROUND OF THE INVENTION

1. Field of the Invention

The method and the apparatus which are the object of the invention relate to the use of eddy currents for detecting faults and discriminating said faults in severity in a passing series of metal tubes.

2. Discussion of the Background

Means of monitoring defects in metal tubes and which resort to eddy currents are already known. Such means comprises a solenoid which is supplied with a current of relatively high frequency which generates an alternating magnetic field. This alternating magnetic field in turn generates eddy currents in the wall of the tube, which interact with the faults present in the form of discontinuities in the metal or alloy to be inspected. These interactions are detected by means of at least one receiving solenoid of which the fluctuations in impedance as the faults pass by are measured. The use of a receiving solenoid comprising two opposing windings makes it possible to enhance the sensitivity of measurement.

In the case of magnetic metals such as carbon steels, these same inspecting means may be used on condition that the metal is saturated with a sufficiently intense continuous magnetic field for its permeability to be reduced to a constant level for a given product and comparable with that of a non-magnetic metal or alloy. In the case of a carbon steel, this permeability is thus virtually brought to the level of that of an austenitic steel.

Thus it is possible to detect faults of relatively small dimensions such as fissures or breaks in cohesion of greater or lesser depth and which may even pass right through the metal and be the source of leakage. Such an inspection is performed continuously by causing the tubes to travel through the solenoids of the detection apparatus which employs eddy currents, at speeds which may be as much as several meters per second.

Experience shows that these inspecting means do not make it possible reliably to identify from all the defects detected, those which are capable of causing leakages through the wall of a tube. Indeed, a surface fault may give a signal the amplitude of which may be equal to or greater than that of a signal corresponding to a fault of relatively considerable depth. Well, generally speaking, tubes having superficial faults may be recovered by some secondary operation or repair while other tubes having deep faults have to be rejected.

For these reasons, it is in many cases necessary to verify the extent of the faults detected by eddy currents by using some other method such as a visual inspection or a hydraulic test for sealing-tightness.

Such hydraulic tests make it possible to establish that only a small proportion of the tubes rejected during the course of eddy current inspections, on account of open faults producing a signal of an amplitude corresponding to that of a standard fault, do actually exhibit leakages under internal fluid pressure.

Attempts have been made to find ways of using eddy current inspection means which make it possible to select from all the faults detected on the walls of metal tubes of all types said faults being either internal faults or faults opening on the outside surface of the tubes those faults which are of relatively substantial depth and distinguish them from superficial faults. It may also happen that the faults or defects open on the inside surface of the tubes, the faults or defects being either internal or opening also on the outside surface of the tubes (going through defects).

In particular, a possible method of determining a rejection threshold has been sought which might with virtual certainty guarantee the rejection of tubes exhibiting faults which pass almost completely through the thickness while not at the same time rejecting a considerable quantity of tubes which suffer from faults opening on the outside surface of the tube of a depth which does not exceed about 10% of the thickness of the tube. Finally, attempts have been made to find a way of carrying out such inspections on tubes having an outside diameter which may be as much as or greater than 200 mm while their thickness may be at least 10% of their diameter, such tubes passing by the inspection means at speeds of several meters per second.

DESCRIPTION OF THE INVENTION

The method and the apparatus which are the object of the invention make it possible to obtain such results.

The method according to the invention resides in passing a metal tube which proceeds continuously, by the immediate vicinity of inspection means employing eddy currents in order to produce interaction between the eddy currents generated in the wall of the tube and any defects therein, said defects being either internal defects or defects opening on the outside surface of the tube, such interaction then being detected and the amplitude of the signals resulting therefrom being measured by known means.

According to the invention, the eddy currents are generated in the wall of the tube by means of two alternative fields of different specific frequencies in the range of medium and high frequencies. For each fault which is capable of being detected, the amplitudes of the signals of interaction of this fault with the eddy currents corresponding to each of these two frequencies are measured, the amplitude $S1$ being that corresponding to the least high frequency while the amplitude $S2$ is that corresponding to the other higher frequency, these amplitudes being expressed in decibels. Then, the difference $D = S2 - S1$ expressed in decibels is determined and the said difference D is compared with a rejection difference Do which is that corresponding to a standard hole pierced from the outside surface of the tube of a given depth which is at least equal to 5% of the thickness of the tube wall and not exceeding 50% of the thickness of the tube wall. Tubes in which D is less than Do are rejected.

Advantageously, for severe applications, for example requiring high internal pressures, the difference Do which constitutes the rejection threshold corresponds to a standard hole of a depth no greater than 20% of the thickness of the tube wall.

Preferably, as the least high frequency of the alternating magnetic field, a given frequency is used which is comprised between 0.5 and 10 Khz and preferably between 1 and 3 Khz. The higher frequency is preferably comprised between 20 and 150 Khz.

When the magnetic metal or alloy tubes are passing by, the inspection is performed by saturating these metals or alloys with a continuous magnetic field generated by a winding traversed by a direct current which surrounds the means of generating alternating magnetic fields and the means of detecting signals corresponding to the interactions between the faults and the eddy currents.

The invention also relates to an apparatus for carrying out the method which has just been described. This apparatus makes it possible to use eddy currents for detecting faults either internal or opening on the outside surface of the tubes existing in the wall of a metal tube which is passing by the apparatus. The apparatus comprises means whereby a metal tube is able to pass by the apparatus at a constant speed and on one axis.

According to the invention, it comprises means of alternating magnetic fields at two different specific frequencies in the range comprising the medium and high frequencies, means of detecting the signals resulting from interactions between each fault and the eddy currents corresponding to each of the two frequencies of the magnetic fields, recording and measuring means making it possible to calculate the difference in decibels $D = S2 - S1$ of the amplitudes expressed in decibels of the signals S2 and S1 respectively obtained at the higher and lower frequencies, and means of comparison which make it possible to establish whether D is greater than or less than a value Do, signalling means making it possible to display a signal for rejection of the tube if D is less than Do.

Preferably, the apparatus comprises means which make it possible to produce two alternating magnetic fields, the frequencies of which are in the range comprised between 0.5 and 10 Khz on the one hand and between 20 and 150 Khz on the other.

The means of generating alternating magnetic fields advantageously comprise either at least one solenoid inside which there is housed at least one detection solenoid, these solenoids having a common axis which is also the axis of passage of the metal tubes to be inspected, or at least one solenoid which performs emission and detection.

Advantageously, the detection solenoid comprises two opposing windings mounted side by side to enhance the sensitivity of detection.

According to a first embodiment, the means of generating the alternating magnetic fields comprise two solenoids disposed one after the other along the axis of passage of the tubes, the first being supplied at the lowest frequency and the second at the highest frequency. Each of these solenoids encloses a detection solenoid connected to the means of measuring the amplitude of the interactions and comparing the difference in decibels between these amplitudes and a rejection value.

These solenoids are advantageously solenoids which enclose the tube to be inspected.

Memorizing means make it possible to store in a memory the amplitude of each signal denoting a fault detected during passage through the first detection solenoid so that it may correspond to the signal relating to this same fault detected upon passage through the second solenoid, the necessary travelling time being taken into account by calculating means.

According to a particular embodiment of the apparatus, it is possible to use a single solenoid for generating alternating magnetic fields by simultaneously energising this solenoid in known manner by means of two current sources of different frequencies. Similarly, a single detection solenoid may be used, discriminating means making it possible to separate and process the signals of interaction of the eddy currents of different frequencies with one and the same fault.

When tubes consisting of magnetic alloys or metals are being inspected, the apparatus comprises a winding the axis of which corresponds to the axis of passage of the tube and which is supplied with direct current in order to generate a magnetic field of a sufficient strength to saturate this metal and brings its permeability to a level comparable with that of a non-magnetic metal or alloy. The dimensions of this winding are determined so that it makes it possible to accommodate both the emission and the detection solenoids.

The method and the apparatus according to the invention are applied to all types of metal or alloy tubes and preferably to those which take the form of a body of revolution. The dimensions of these tubes are preferably less than or equal to 200 mm in outside diameter with wall thickness of 1 to 20% of the diameter, the thickness preferably being limited to 20 mm.

Many modifications may be made to the method and to the apparatus according to the invention without departing from the scope thereof.

The examples and drawings which follows describe in a non-limitative manner particular embodiments of the apparatus according to the invention.

Figure 3:
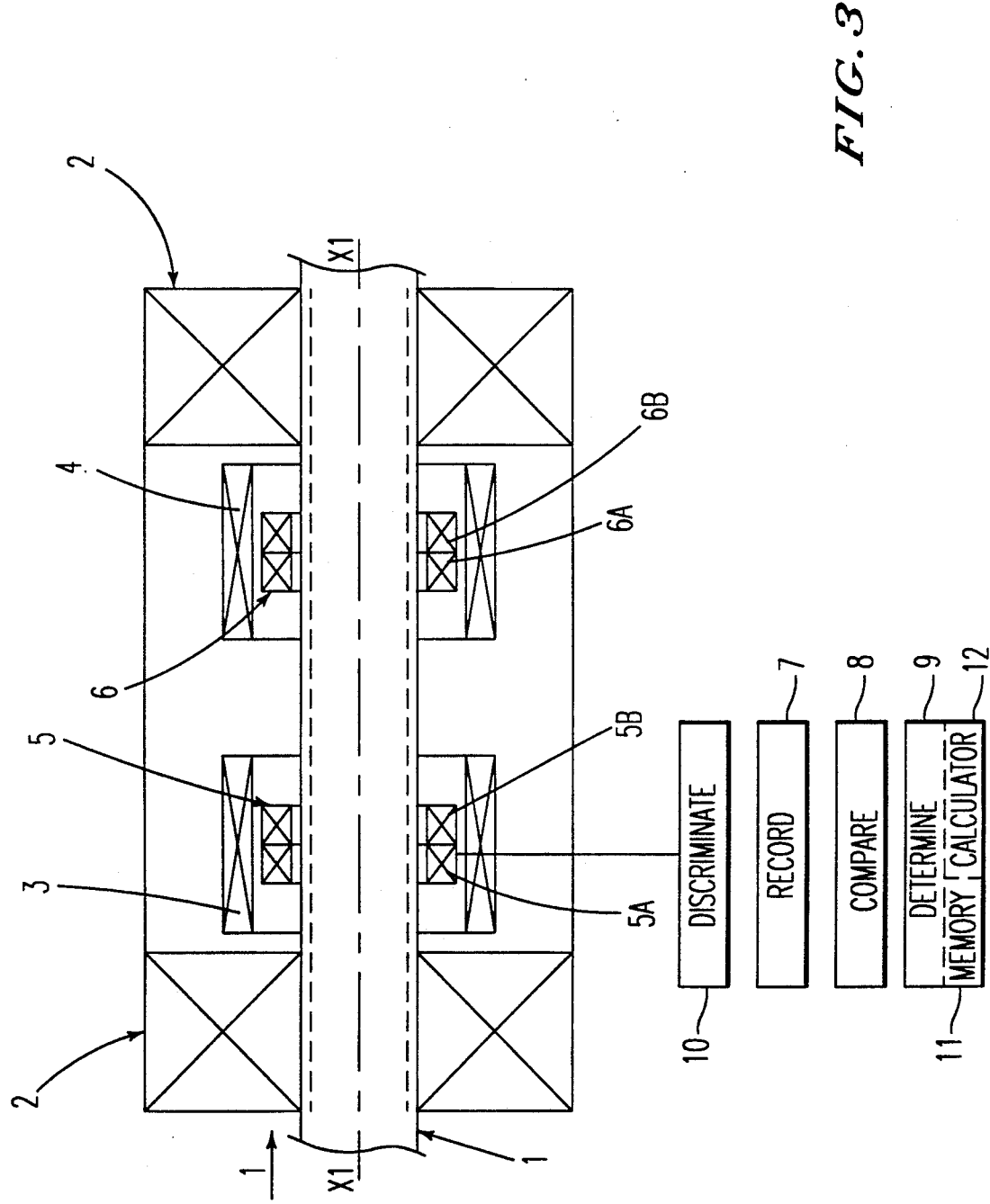

FIG. 3 is a purely diagrammatic overall view of an apparatus for carrying out the method according to the invention. It relates to the inspection of a carbon steel tube of revolution of which only a portion 1 is shown, this being disposed according to the axis of movement X1—X1. Arrow F represents a means of passing the tube through the apparatus. As can be seen from FIG. 1 the passage through which the tube passes conforms closely to the outer diameter of the tube. Element 7 represents a means for recording measured signals, element 8 represents a means for comparing signals received by the detection solenoids 5 and 6. Element 9 represents a means for determining when to reject a tube based upon the compared signal.

The said tube is displaced along this axis X1—X1 in the direction of the arrow F at a constant speed within a range comprised between 1 and 20 meters per second. The inspection is performed at a temperature which is close to ambient temperature. A solenoid 2 disposed according to the same axis X1—X1 is supplied with direct current by means not shown in order to generate a direct current magnetic field the intensity of which is determined in order to saturate the tube 1 in the interior of the solenoid 2. The residual permeability of the tube 1 in this zone is thus close to that of an austenitic steel.

The two solenoids 3 and 4 each generate an alternating magnetic field, of which the different frequencies are in the range of the medium and high frequencies, the frequency of the field generated by the solenoid 3 being less than that of the solenoid 4. These two solenoids are disposed one after the other on the axis X1—X1 and are connected to current sources, not shown. The frequency of the field generated by the solenoid 3 is selected within the range comprised between 0.5 and 10 Khz and that of the solenoid 4 between 20 and 150 Khz. Housed inside the solenoid 3 is a detection solenoid 5 comprising two windings 5A, 5B side by side, of axis X1—X1, mounted in opposition. Similarly, mounted inside the solenoid 4 is the second detection solenoid 6 which comprises two windings 6A, 6B mounted side by side in opposition and on the axis X1—X1. These two detection solenoids 5, 6 are connected in known manner to known means of measuring impedance which make it possible to detect the fluctuations in impedance produced by the passage of a fault located in the wall of the tube 1, said fault being either an internal fault or a fault opening on the outside surface of the tube. These fluctuations in impedance result from interactions between this fault and the eddy currents created by the alternating magnetic fields existing in the solenoids 3 and 4. These fluctuations in impedance are, at the level of the measuring means, not shown, translated into a signal the amplitude of which is expressed in decibels. For each fault detected by the solenoid 5, a signal S1 is obtained and for the same fault, a signal S2 upon passage through the solenoid 6. Memorizing means make it possible to store the signal S1 in a memory so that it can be compared with the signal S2 at the moment when it is detected by the solenoid 6, delay means taking into account the distance between the two solenoids and the speed of passage making it possible accurately to compare the two signals S1 and S2 which belong to one and the same fault.

Figure 1:
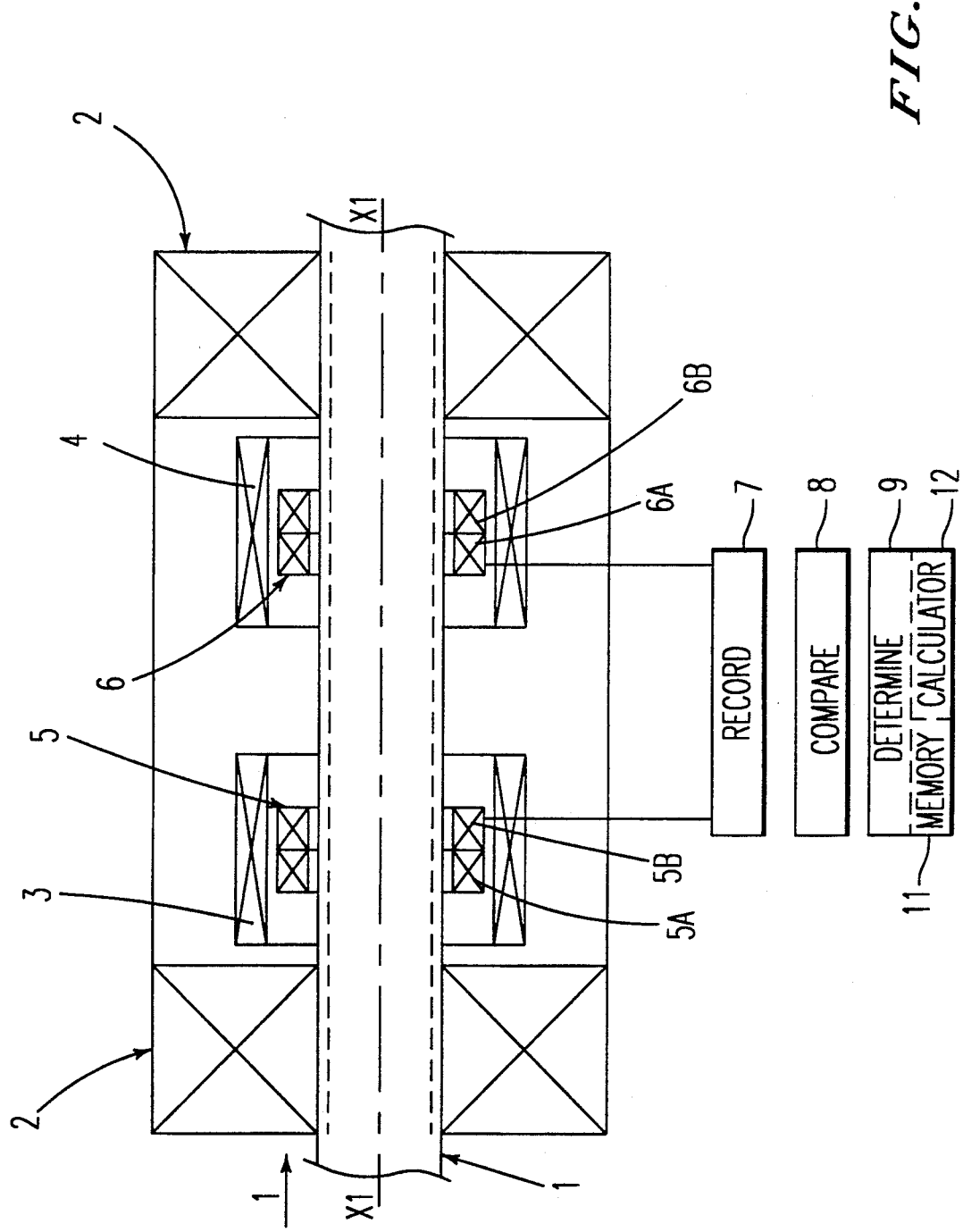
FIG. 1 is a diagrammatic overall view of an embodiment of the apparatus according to the invention.

Calculating means make it possible to determine the difference $D = S2 - S1$ expressed in decibels and compare it with a rejection difference Do which corresponds to the signals detected upon passage of a standard hole made in the wall of a tube passing through the apparatus in FIG. 1.

Figure 2:
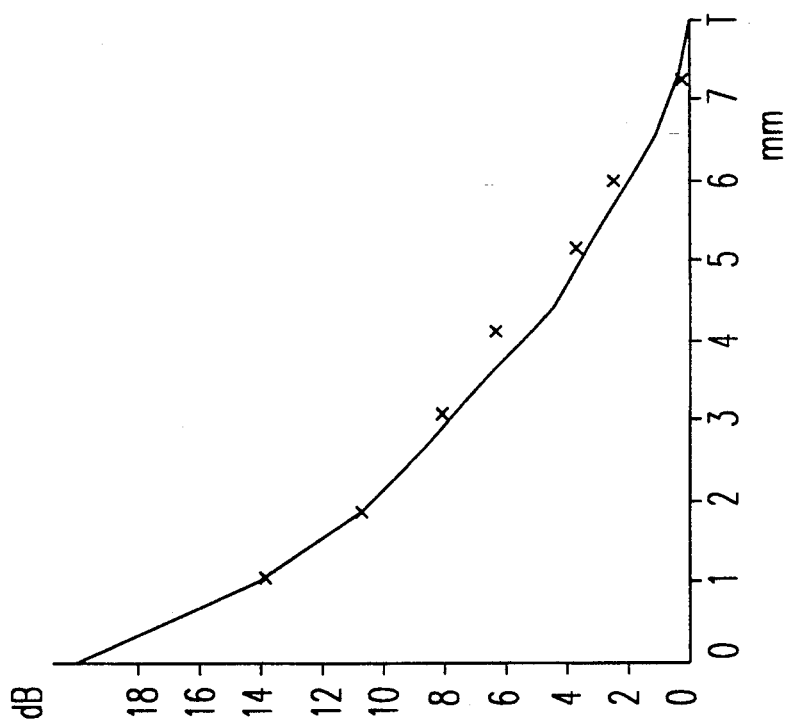
FIG. 2 shows a graph which makes it possible to determine the rejection thresholds of tubes as a function of the acceptable fault depth.

FIG. 2 shows a graph showing the fluctuation in D as a function of the depth of penetration of the outside wall of a tube of standard holes of the same diameters orientated in a radial direction. In the case of this drawing, the holes are 4 mm in diameter, are flat-bottomed and pierced from the outside surface into a wall 8 mm thick of a carbon steel tube with an outside diameter of 60 mm. For drawing this graph, the frequency of the magnetic field generated by the solenoid 3 is 1.6 Khz and the frequency of the magnetic field generated by the solenoid 4 is 60 Khz. In FIG. 2, the depths of penetration in millimeters are shown on the abscissa while the difference in decibels $D = S2 - S1$ are shown on the ordinates. The amplification of the signals S1 and S2 is adjusted so that for a through hole of a depth equal to 8 mm the amplitudes of S1 and S2 are equal, D then being equal to 0. As a function of the applications of the tubes, so as value Do corresponding to a standard hole of relatively shallow depth is chosen as the rejection threshold or difference. Thus, as the graph shows, a fault of only 1 mm depth corresponds to a difference D1 of 14 decibels. By choosing this difference D1 as a rejection level, one is virtually sure of not letting through faults of a depth greater than 1 mm, subject to rejection of all tubes which have faults having differences D less than D1. FIG. 3 shows a second embodiment of the present invention which includes only a single energizing solenoid 3 which may be driven at two separate frequencies. Elements 1, 2, 5, 5a, 5b, 7, 8 and 9 correspond to those discussed for FIG. 1. Element 10 is a discrimination means for discriminating the two frequencies of the signal picked up by pick-up coils 5, 5a and 5b.

What is claimed:

1. A method of detecting the depth of faults which exist in the wall of a metal tube, comprising the steps of: passing the tube through a passage, the passage having inner walls which conform to an outer surface of the tube;

generating eddy currents in the wall of the tube by means of two alternating fields of different specific frequencies, including a lower and a higher frequency;

measuring amplitudes of signals resulting from interactions of a fault with the eddy currents corresponding to each of these two frequencies, an amplitude S1 corresponding to the lower frequency and an amplitude S2 corresponding to the higher frequency by means of respective first and second detection solenoids disposed along the passage;

storing amplitudes of detected signals S1 and S2 from the first and second detection solenoids in a memory, wherein the signal from the first detection solenoid is received earlier than the signal from the second detection solenoid by a time equal to a transit time for a point on the tube to move from the first detection solenoid to the second detection solenoid;

comparing the stored amplitude signal S2 of the second detection solenoid with the stored amplitude signal S1 from the first detection solenoid and determining a difference $D = S2 - S1$ for a defect; and comparing D with a rejection threshold or difference Do which corresponds to a standard fault on a surface of the tube, said standard fault having a depth which is at least 5% of the thickness of the tube wall and not greater than 50% of the thickness of the tube wall, wherein a tube comprising at least one fault having a difference D less than Do is rejected.

2. A method according to claim 1, wherein the rejection threshold or difference Do is employed which corresponds to a standard hole pierced from the outside surface of the tube of a depth not exceeding 20% of the thickness of the tube wall.

3. A method according to claim 1, characterised in that the lower frequency of the alternating magnetic fields is between 0.5 and 10 Khz while the higher is between 20 and 150 Khz.

4. A method according to claim 3, characterised in that the lower frequency of the alternating magnetic field is between 1 and 3 Khz.

5. An apparatus for using eddy currents to detect the depth of faults existing in the walls of a passing stream of metal tubes, said faults being either internal faults or faults opening on the outside surface of the tube, comprising:

means for passing a metal tube at a constant speed through a passage which conforms to the tube diameter;

means for generating alternating magnetic fields at a lower and a higher frequency, in the vicinity of the tube;

detecting means comprising first and second detection solenoids for detecting signals S1 and S2 resulting from the interaction between each fault and the eddy currents corresponding to each of the two frequencies of the magnetic fields, memory means for storing in a memory, detected amplitudes of the signals from the first and second detection solenoids, means for comparing the stored amplitude S2 of the second detection solenoid with the stored amplitude S1 signal from the first detection solenoid which is received earlier than the signal from the second detection solenoid by a time equal to a transit time for a point on a tube to move from the first detection solenoid to the second detection solenoid and means for calculating a difference $D = S2 - S1$ of the amplitudes of the signals S2 and S1 obtained for a defect respectively at the higher and lower frequencies;

means for determining whether D is less than a value Do which constitutes a rejection threshold; and signalling means for displaying a tube rejection signal when D is less than Do.

6. An apparatus according to claim 5, wherein said means for generating alternating magnetic fields produce a lower frequency of between 0.5 Khz and 10 Khz and a higher frequency of between 20 and 150 Khz.

7. An apparatus according to claim 6, wherein said first and second detection solenoids have a common axis which is an axis of passage of the metal tubes which are to be inspected.

8. An apparatus according to claim 7, wherein each of the first and second detection solenoids comprise two windings mounted side by side and in opposition.

9. An apparatus according to claim 7, characterized in that the means for generating alternating magnetic fields comprise two solenoids disposed one after the other along the axis of passage and supplies in the first case at the lower frequency and in the second case at the higher frequency; each of these two solenoids enclosing said first and second detection solenoids.

10. An apparatus according to one of claims 7 to 9, wherein the solenoids enclose the tube to be inspected.

11. The apparatus according to claim 5, wherein the means for generating alternating magnetic fields comprises only one solenoid which is energized simultaneously by two current sources of different frequencies; and further comprising discriminating means for separating the signals for interaction of eddy currents of different frequencies with one and the same fault.

12. A method according to claim 1, wherein:

the tubes inspected are tubes of revolution and have an outside diameter less than 200 mm, their wall thickness being between 1 and 20% of their diameter.

13. A method according to claim 1, comprising the further step of:

magnetically saturating with a continuous magnetic field, the metal tube when said metal tube is made from a magnetic alloy or magnetic material.

14. An apparatus according to claim 5, further comprising:

a winding means for providing a magnetic field of a sufficient strength to magnetically saturate a metal or alloy of the metal tube and bring the permeability of the metal or alloy of the metal tube to a level comparable with that of a non-magnetic metal or alloy, the dimensions of said winding means accommodating both said means for generating alternating magnetic fields and said first and second detection solenoids.

* * * * *